United States Patent [19]

Tsutsui et al.

[11] Patent Number: 4,928,297
[45] Date of Patent: May 22, 1990

[54] RADIOGRAPHIC DIAGNOSTIC APPARATUS

[75] Inventors: Hiroshi Tsutsui, Yawata; Sueki Baba, Suita; Koichi Ohmori, Toyonaka; Osamu Yamamoto, Moriguchi; Hiroshi Watanabe, Yawata, all of Japan

[73] Assignee: Matsushita Electric Industrial Co., Ltd., Osaka, Japan

[21] Appl. No.: 184,829

[22] Filed: Apr. 22, 1988

[30] Foreign Application Priority Data

Apr. 22, 1987 [JP] Japan .................. 62-98956

[51] Int. Cl.⁵ .............................................. G21K 5/10
[52] U.S. Cl. ...................................... 378/146; 378/197
[58] Field of Search .......................... 378/146, 197

[56] References Cited

U.S. PATENT DOCUMENTS

| | | | |
|---|---|---|---|
| 4,355,409 | 10/1982 | Amplatz | 378/146 |
| 4,464,777 | 8/1984 | Machida | 378/146 |
| 4,490,835 | 12/1984 | Wons | 378/146 |
| 4,493,098 | 1/1985 | Riihimaki et al. | 378/146 |
| 4,709,382 | 11/1987 | Sones | 378/146 |

OTHER PUBLICATIONS

"Digital Radiography of the Chest: Clinical Experience with a Prototype Unit," Fraser et al., Diagnostic Radiology, vol. 148, No. 1, pp. 1-5 (Jul. 1983).

"Slot-Technik: Verbesserte Bildqualitat bei reduzierter Strahlenbelastung," Grotemeyer et al., Rontgenpraxis, 35, pp. 186-189 (1982).

Richard Moore et al., Applied Radiology, issued Nov.-Dec., 1977; p. 85.

*Primary Examiner*—Craig E. Church
*Attorney, Agent, or Firm*—Spencer & Frank

[57] ABSTRACT

A radiographic diagnostic apparatus including an X-ray tube for generating X-ray radiation, a line slit for shaping the X-ray radiation into a fan beam, a linear X-ray sensor array for detecting the X-ray radiation, and apparatus for driving the components is provided. The focal spot of the X-ray tube and the line slit are disposed on a straight line that connects between a specified fixed point and the center of the linear sensor array of a line extending therefrom. The X-ray tube, the line slit and the linear X-ray sensor array are driven together in a direction perpendicular to the direction of alignment of the linear X-ray sensor array so as to scan an object and thereby produce a radiographic image of the object.

4 Claims, 5 Drawing Sheets

RADIOGRAPHIC DIAGNOSTIC APPARATUS

BACKGROUND OF THE INVENTION

1. Field of the Invention:

The present invention relates to a radiographic diagnostic apparatus which employs a radiographic sensor array.

2. Description of Related Art:

Radiographic images may be electronically produced without using X-ray films by using either a combination of an image intensifier (a fluoroscopic intensifier) and a camera tube or a linear X-ray sensor array. The radiographic technique that utilizes a linear X-ray sensor array employs an X-ray fan beam which is obtained by passing a primary form of radiation through a slit. This can remove scattered radiation from an object and in that way provide good-quality images. Further, it can be equipped with a screen which is larger than the type employed with image intensifiers. Thus, an increasing future demand therefor is anticipated.

Radiographic techniques that involve driving of a linear X-ray sensor array include one techniqus in which, while an X-ray tube is being rotated around a focal spot thereof, a line slit and the linear X-ray sensor array are moved in parallel with each other or rotated together in synchronization with the rotation of the X-ray tube so as to scan the object and produce an image thereof. This is an application of a technique called moving-slot radiography that employs films, and is described on page 85 in the publication Applied Radiology, the issue dated November–December 1977, and on page 783 in the publication Radiology, Vol. 128, 1978. In these publication the method of moving-slot radiographic is described, in which an object is irradiated with the X-ray fan beam, and a radiographic image thereof is produced by scanning the object by the linear sensor array which is moved in synchronization with the sweep of the fan beam without using any photographic film.

FIG. 8 shows the principle of the above-described known type of radiography. X-rays irradiated from a focal spot 2 of an X-ray tube 1 are shaped into a fan beam by a line slit 3, and the fan beam is detected by a linear X-ray sensor array. While the X-ray tube 1 is being rotated, the line slit 3 and the linear X-ray sensor array 4 are moved in the direction indicated by the arrows in synchronization with the rotation, of the X-ray tube 1 so as to produce a radiographic image of the object interposed between the line slit 3 and the linear X-ray sensor array 4.

The output capacity of the X-ray tube required for the above-described radiography will be considered. Assuming that the surface to be scanned by the sensor array is divided into 1000 lines, then a time which is 1000 times as long as that required to produce an image on a film surface is necessary. For example, if the time for scanning a single line is 100msec, then the time required to produce an image on a flat film surface is 100 msec×1000, i.e., 10 sec. Conversely, in order to scan 1000 lines in the same period of time, an X-ray output which is 1000 times as high as that required for conventional radiography is necessary. Thus, radiography which employs a linear X-ray sensor array requires an X-ray tube of excessively large capacity.

In order to obviate the above-described problem, the X-ray tube and the linear sensor array could be brought closer to each other so as to increase the dose of X-ray radiation. However, this will cause the following disadvantages. FIGS. 9a and 9b illustrate the principle involved when the X-ray tube is brought closer to the sensor. The two views are respectively taken from the side and the end of the linear sensor array 4. When the X-ray tube 1 and the focal spot 2 are respectively moved to the positions indicated by 1' and 2', the angle formed when the surface to be scanned is viewed from the focal spot 2 increases to the angle formed when the surface to be scanned is viewed from the focal spot 2', as shown in the drawings. As a result, the magnification factor and hence the degree of distortion of the image of the object 7 so produced increases in the vicinity of the ends of the screen, making it difficult to extract diagnostic information from the image produced.

SUMMARY OF THE INVENTION

Accordingly, an object of the present invention is to provide a radiographic diagnostic apparatus which is capable of increasing the output of an X-ray tube when the X-ray tube is brought closer to an object without increasing the output of the X-ray tube and without generating distortion in the image produced.

To this end, the present invention provides a radiographic diagnostic apparatus including an X-ray tube for generating X-ray radiation, a line slit for shaping the X-ray into a fan beam, a linear X-ray sensor array for detecting the X-ray radiation, and driving means for these components, the apparatus being characterized in that the focal spot of the X-ray tube and the line slit are disposed on a straight line that connects between a specified fixed point and the center of the linear sensor array or a line extending therefrom, and that the X-ray tube, the line slit, and the linear X-ray sensor array are driven together in a direction perpendicular to the direction of alignment of the linear X-ray sensor array so as to scan an object and thereby produce an radiographic image of the object.

In the thus-arranged radiographic diagnostic apparatus, the dose of radiation irradiated on the object can be increased without increasing the output of the X-ray tube when the X-ray tube is moved toward the object by a distance which corresponds to the thickness of the object. This produces a radiographic image which is not that obtained by irradiation from the focal spot of the X-ray tube but close to that obtained by irradiation from the fixed point, and the degree of image distortion which results from the shifting of the position of the X-ray tube can thus be reduced.

DESCRIPTION OF THE PREFERRED EMBODIMENTS

The present invention will be hereinunder described by way of example with reference to the accompanying drawings.

Figure 1:
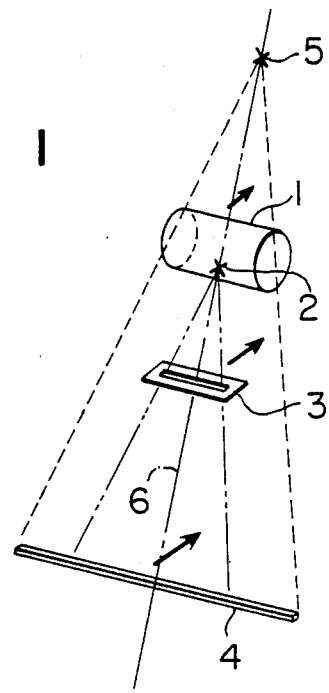
FIG. 1 illustrates the basic principle of the present invention.

Referring first to FIG. 1 which illustrates the basic principle of the present invention, a focal spot 1 of an X-ray tube 1 and a line slit 3 are disposed on a line 6 which connects between a fixed point 5 and the center of a linear X-ray sensor array 4 in the order shown in the drawing. They are made movable on the line 6 between the positions thereof represented in the drawing and the position of the linear X-ray sensor array 4. The X-ray tube 1, the line slit 3 and the linear X-ray sensor array 4 are driven for scanning in the direction indicated by the arrows with the fixed point 5 serving as the center of this movement.

Figure 2:
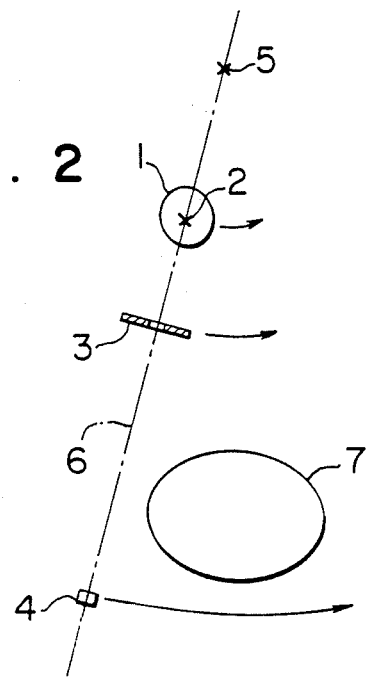
FIG. 2 illustrates the driving method of a first embodiment of a radiographic diagnostic apparatus according to the present invention.

FIG. 2 illustrates a driving method for the first embodiment, in which the apparatus of FIG. 1 is viewed from an end of the linear X-ray sensor array 4. The X-ray tube 1, the line slit 3 and the linear X-ray sensor array 4 are rotated around the fixed point 5 in the direction indicated by the arrows so as to scan the object. Even if the X-ray tube is moved to a position closer to the sensor array, the direction in which the X-ray radiation is made incident on the linear sensor array remains the same on the central line 6 in the sensor array, resulting in production of a radiographic image which has, in terms of distortion, the same characteristics as those of a radiographic image obtained when the focal spot 2 of the X-ray tube 1 is located at the fixed point 5, that is, which has a smaller degree of distortion.

Figure 3:
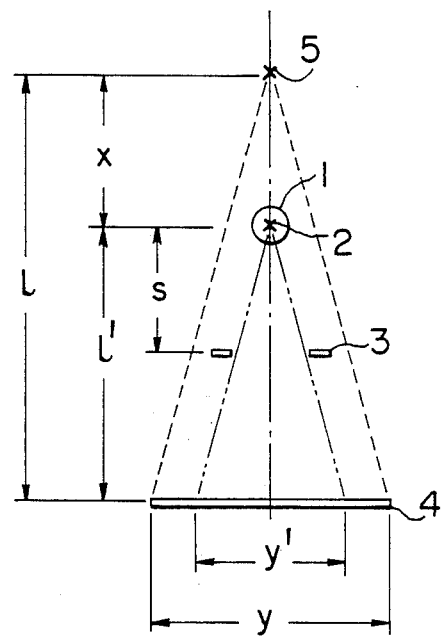
FIG. 3 illustrates the positional relationship of the first embodiment of the present invention.

FIG. 3 illustrates the positional relationship of the first embodiment of the present invention. The length of the central line which extends between the fixed point 5 and the linear X-ray sensor array 4 is designated by l. If the intensity of X-ray radiation incident on the linear X-ray sensor array 4 from the X-ray tube 1 whose focal spot 2 is located at the fixed point 5 is $I_0$, the intensity of X-ray radiation $I_1$ from the X-ray tube 1 which has been brought closer to the linear X-ray sensor array by distance x is expressed by the following equation:

$$I_1 = (l/l^1)^2 I_0 \quad (1)$$

Since $l^1 = l - x$, Equation (1) is transformed as follows:

$$I_1 = (l/l-x)^2 I_0 \quad (2)$$

For example, if the focal spot 2 of the X-ray tube 1 is at the mid-point of the way between the fixed point 5 and the linear X-ray sensor array 4, i.e., if $$x = \tfrac{1}{2}l,$$

the intensity of the radiation $I_1$ is four times larger than $I_0$.

In a case where the X-ray radiation irradiated from the X-ray tube 1 located at the fixed point 5 is stopped down by the line slit 3 so that it irradiates the overall length y of the linear X-ray sensor array, if only the X-ray tube 1 is moved toward the linear X-ray sensor array 4 in a state wherein the line slit 3 is being fixed, the irradiation range becomes wider than y, resulting in production of a radiographic image which is more and more distorted as the distance from the center line increases. On the other hand, if the X-ray tube 1 is moved together with the line slit 3 by the distance x, and with the distance S between the focal spot 2 of the X-ray tube 1 and the line slit 3 (which is set when the focal spot 2 is located at the fixed point 5), being fixed, the X-ray beam is irradiated throughout a range y' which is expressed by the following equation.

$$y' = \left(\frac{l^1}{l}\right) y = \left(\frac{l-x}{l}\right) y \quad (3)$$

In other words, when the X-ray tube 1 is at a position closer to the sensor array, the irradiation range becomes narrower. However, since the shape of the X-ray fan beam incident on the linear X-ray sensor array 4 is similar to that obtained when the X-ray tube is located at its original fixed position, the degree of distortion of the resultant radiographic image can be reduced.

Figure 4:
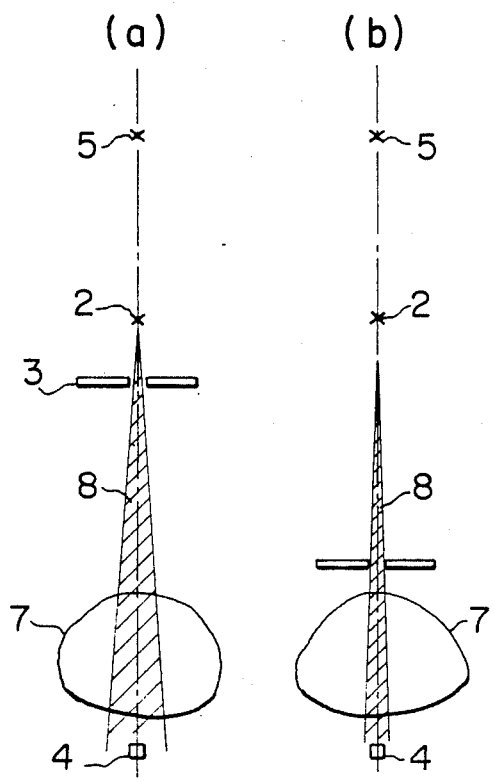
FIG. 4 is a cross-sectional view, showing changes in the width of an X-ray fan beam.

FIG. 4(a) and FIG. 4(b) illustrates changes in the width of the X-ray fan beam obtained when the X-ray tube is moved. FIG. 4(a) denotes a case where only the focal spot 2 of the X-ray tube is brought closer to the sensor array while the line slit 3 is fixed. A radiation width 8 indicated by the hatched portion then becomes larger, and the dose of the scattered radiation is accordingly increased. Thus, reduction in the dose of scattered radiation which is the advantage of this radiographic technique does not occur. FIG. 4(b). (b) denotes a case where the focal spot 2 of the X-ray tube is moved together with the line slit 3 with the distance between them being fixed. In this case, the shape of the X-ray beams is similar to that obtained when the focal-spot 2 is located at its original position. The width of the radiation that traverses the object becomes smaller, and the amount of scattered radiation is thereby reduced. In this way, the advantage of this method is further enhanced.

Figure 5:
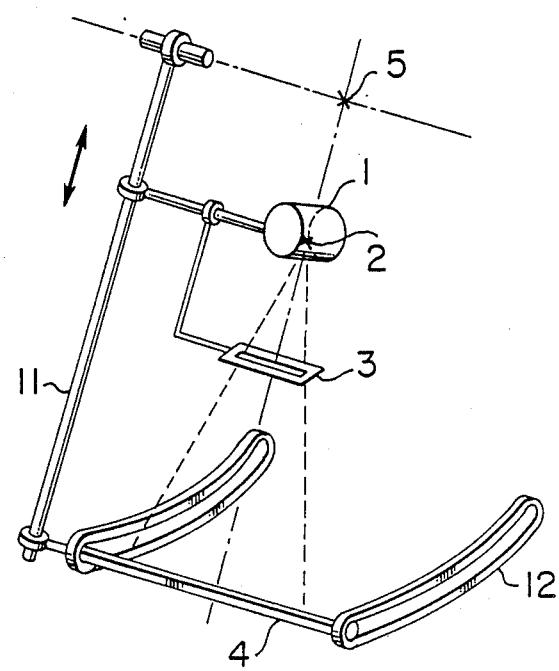
FIG. 5 is a perspective view of the essential parts of the first embodiment of the present invention.

FIG. 5 illustrates a driving method of the first embodiment of the present invention. The X-ray tube 1, the line slit 3 and the linear X-ray sensor array 4 are fixed to an shaft 11, and these components are moved in such a manner as to rotate around the fixed point 5 for scanning the object. The linear X-ray sensor array 4 is moved along guides 12 having a curvature so that it is not shifted from its position relative to the X-ray tube 1. The X-ray tube 1 and the line slit 3 are movable in the direction indicated by the arrow.

According to the present invention, the overall portion of the object to be exposed to the radiation is first exposed to X-ray radiation irradiated from the focal spot 2 of the X-ray tube 1 located at the fixed point 5 so as to produce a screening image of the object. Next, a portion of interest of the object is screened, and is exposed to the radiation irradiated by the X-ray tube 1 which has been moved together with the line slit 3 toward the linear X-ray sensor array so as to increase the dose exposed to the object of X-ray radiation and thereby produce an X-ray radiographic image which offers a large amount of information on the object.

Figure 6:
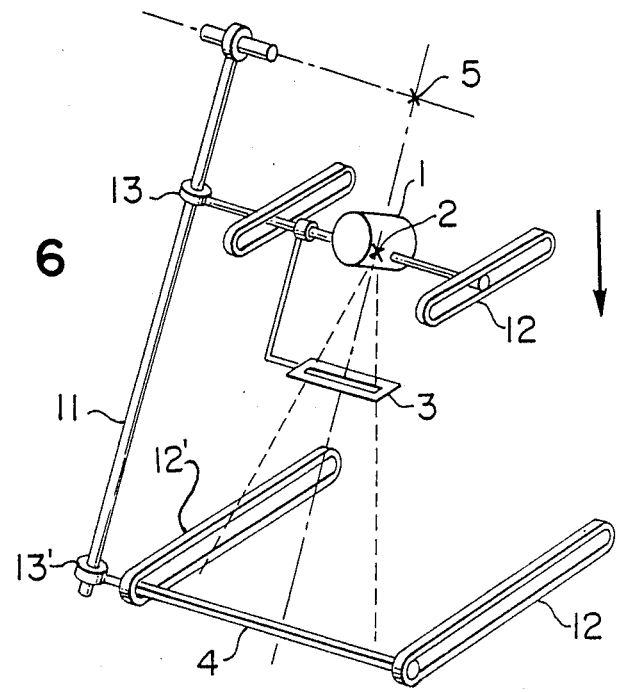
FIG. 6 is a perspective view of the essential parts of another embodiment of the present invention.

FIG. 6 shows the driving method of another embodiment of the present invention. This involves linear movement of the X-ray tube 1 and the linear X-ray sensor array with the fixed point serving as the center of the rotational movement of the line containing the X-ray tube 1 and the linear X-ray sensor array 4. The X-ray tube 1 and the linear X-ray sensor array 4 are coupled to the shaft 11 through sliding bearings 13 and 13', respectively. The X-ray tube 1 and the linear sensor array 4 are moved on straight lines along guides 12 and 12' while changing the positions thereof relative to the shaft by means of the bearings 13, 13', by rotating the shaft about an axis which passes through the fixed point 5.

Figure 7:
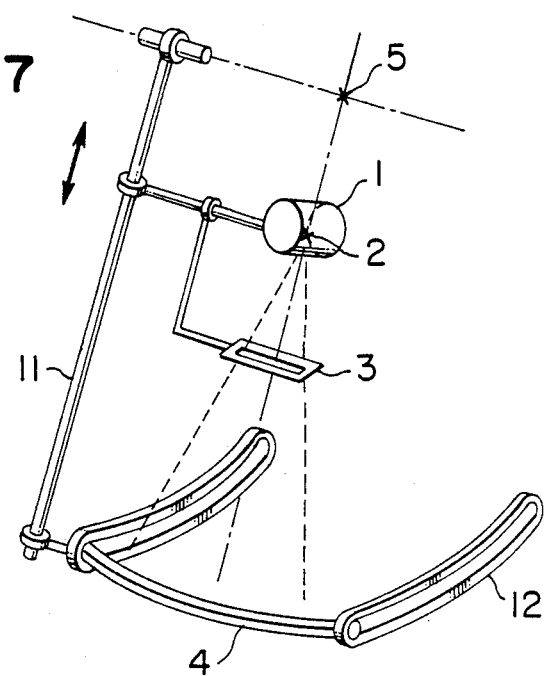
FIG. 7 is a perspective view of another example of a linear X-ray sensor that can be incorporated in the present invention.
Figure 8:
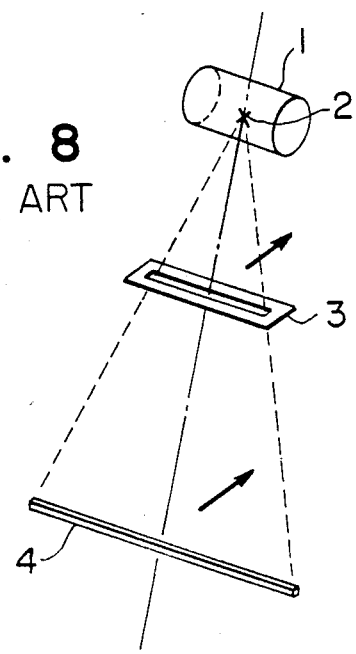
FIGS. 8 and 9 illustrate the operational principle of a known radiograph technique.
Figure 9A:
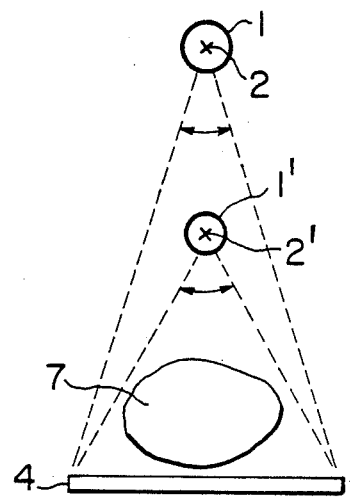
Figure 9B:
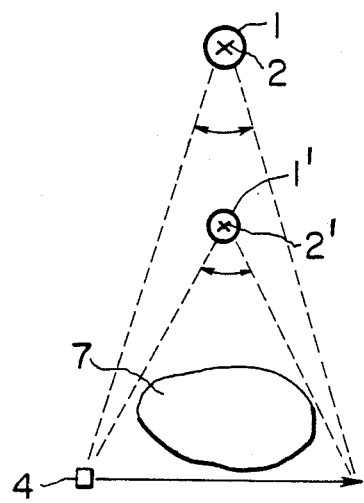

FIG. 7 illustrates another example of a linear X-ray sensor array of the present invention. This linear X-ray sensor array is shaped as an arc of a circle whose center is at the fixed point 5. When the linear X-ray sensor array is formed in this manner, the degree of distortion (caused by the difference in magnification factors) that occurs in the vicinity of the ends of a resultant image can be reduced.

In the radiographic diagnostic apparatus of the present invention, the focal spot of the X-ray tube 1 and the line slit 3 are made movable as a unit on the straight line that connects between the specific fixed point and the center of the linear X-ray sensor array. An X-ray radiographic image of the object is produced by scanning the object which is achieved by moving the X-ray tube 1, the line slit 3 and the linear X-ray sensor array on straight lines or on the arc with the fixed point serving as the center of this movement. When the X-ray tube is moved toward the linear X-ray sensor array by a distance which corresponds to the thickness of the object, the amount of X-ray radiation can be increased without increasing the output of the X-ray tubes 1. At this time, the distortion of a resultant image which is caused by this movement of the X-ray tube 1 can be reduced, and the amount of scattered radiation within the object can be reduced.

Thus, the present invention makes it possible to obviate the problems of the conventional radiography techniques which employ a linear X-ray sensor array. It is therefore possible, according to the present invention, to increase the output capacity of an X-ray tube 1 by using an X-ray tube which has a small output capacity and thereby reduce the overall size of the radiographic diagnostic apparatus provided with improved functions and a reduced production cost.

What is claimed is:

1. A radiographic diagnostic apparatus comprising:
    an X-ray tube for generating X-ray radiation, said X-ray tube having a focal spot,
    a line slit for shaping said X-ray radiation into a fan beam, said line slit extending in a direction of alignment,
    a linear X-ray sensor array for detecting said X-ray radiation, and
    movable means for rotating said X-ray tube, said line slit, and said linear X-ray sensor array about a specified fixed point so as to maintain alignment of said X-ray tube, said line slit, and said linear X-ray sensor array relative to said specified fixed point such that said focal spot of said X-ray tube and said line slit are disposed on a straight line which passes through said specified fixed point and a predetermined portion of said linear sensor array, such that said X-ray tube, said line slit and said linear X-ray sensor array move together in a direction perpendicular to the direction of alignment of said linear X-ray sensor array to scan an object, said focal spot of said X-ray tube being spaced from said specified fixed point, and such that a radiographic image of the object can be produced from an output of said linear X-ray sensor array; and
    said X-ray tube and said line slit are movable along said straight line connecting said fixed point and said predetermined portion of said linear X-ray sensor array.

2. A radiographic diagnostic apparatus according to claim 1, wherein said linear sensor array has a shape which corresponds to the arc of a circle whose center is at said specified fixed point.

3. A radiographic diagnoystic apparatus according to claim 1, wherein the distance between said X-ray tube and said line slit is a predetermined fixed distance.

4. A radiographic diagnostic apparatus, comprising:
    an X-ray tube for generating X-ray radiation, said X-ray tube having a focal spot,
    a line slit for shaping said X-ray radiation into a fan beam, said line slit extending in a direction of alignment,
    a linear X-ray sensor array for detecting said X-ray radiation,
    movable means for maintaining alignment of said X-ray tube, said line slit, and said linear X-ray sensor array relative to a specified fixed point so as to maintain alignment of said X-ray tube, said line slit, and said linear X-ray sensor array relative to said specified fixed point such that said focal spot of said X-ray tube and said line slit are disposed on a straight line which passes through said specified fixed point and a predetermined portion of said linear sensor array, such that said X-ray tube, said line slit and said linear X-ray sensor array move together in a direction having a component which is perpendicular to the direction of alignment of said linear X-ray sensor array to scan an object, said focal spot of said X-ray tube being spaced from said specified fixed point, and such that a radiographic image of the object can be produced from an output of said linear X-ray sensor array;
    said X-ray tube, said line slit, and said linear X-ray sensor array are caused to be aligned along said straight line in sequence from said fixed point and are driven by said movable means for maintaining alignment, such that they have translational motion; and
    said X-ray tube and said line slit are movable along said straight line connecting said fixed point and said predetermined portion of said linear X-ray sensor array.

* * * * *